US00PP15388P2

(12) United States Plant Patent
Olesen et al.

(10) Patent No.: US PP15,388 P2
(45) Date of Patent: Nov. 30, 2004

(54) ROSE PLANT NAMED 'POULEN012'

(50) Latin Name: *Rosa hybrid*
Varietal Denomination: Poulen012

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/812,758

(22) Filed: Mar. 29, 2004

(51) Int. Cl.[7] ..... A01H 5/00
(52) U.S. Cl. ..... Plt./137
(58) Field of Search ..... Plt./137

*Primary Examiner*—Anne Marie Grunberg
*Assistant Examiner*—Annette H Para

(57) ABSTRACT

A new garden rose plant of the hybrid tea class which has abundant, pink flowers and attractive foliage. This new and distinct variety has shown to be uniform and stable in the resulting generations from asexual propagation.

2 Drawing Sheets

Botanical classification: *Rosa hybrid.*
Variety denomination: 'Poulen012'.

SUMMARY OF THE INVENTION

The present invention constitutes a new and distinct variety of garden rose plant which originated from a controlled crossing between a female parent 'Poulsyng', described and illustrated in the abandoned U.S. Plant patent application Ser. No. 09/268,299 dated Mar. 16, 1999, the male parent, an unnamed seedling. The two parents were crossed during the summer of 1995 and the resulting seeds were planted in a controlled environment in Fredensborg, Denmark. The new variety is named 'Poulen012'.

The new variety may be distinguished from its female seed parent, 'Poulsyng' by the following combination of characteristics:

1. While the seed parent 'Poulsyng' has flower petals which are Red Group 36D, 'Poulen012' has flower petals which are White Group 155B with a strong overlay of Reg Group 36D to Reg Group 49D.
2. While the seed parent 'Poulsyng' has 34 to 40 petals 'Poulen012' has 45 to 50 petals.
3. While 'Poulsyng' has basal petal spots which are Yellow Group 3B in color, 'Poulen012' has petal spots which are Yellow Group 6C in color.

The new variety may be distinguished from its pollen parent, an unnamed seedling, by the following combination of characteristics:

1. No petal spots observed on the pollen parent. 'Poulen012' has Yellow Group 6C petal spots.
2. Flowers of the pollen parent produce less fragrance than flowers of 'Poulen012'.

The objective of the hybridization of this rose variety was to create a new and distinct variety for garden use with unique qualities, such as:

1. Uniform and abundant pink flowers;
2. Vigorous, but compact growth when propagated both as a budded rose and on its own roots;
3. Disease resistance;
4. Exceptional flower fragrance.

This combination of qualities is not present in previously available commercial cultivars of this type, known to the inventors, and distinguish 'Poulen012' from all other varieties of which are aware.

As part of their rose development program, L. Pernille Olesen and Mogens N. Olesen germinated the seeds from the aformentioned hybridization during winter of 1995 and conducted evaluations on the resulting seedlings in a controlled environment in Fredensborg, Denmark.

'Poulen012' was selected in the spring 1996 by the inventors as a single plant from the progeny of the aforementioned hybridization.

Asexual reproduction of 'Poulen012' by traditional budding and rooted cuttings was first done by L. Pernille and Mogens N. Olesen in their nursery in Fredensborg, Denmark in July, 1996. This initial and other subsequent asexual propagations conducted in controlled environments have demonstrated that the characteristics of 'Poulen012' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulen012'. Specifically illustrated in SHEET 1:

FIG. 1.1; Open flower above view, open flower side view with attachment of receptacle, sepals, and peduncle;

FIG. 1.2; Flower bud closed, flower bud as sepals unfold;

FIG. 1.3; Flower petals, detached;

Specifically illustrated in SHEET 2:

FIG. 2.1; Sepals, receptacle, and peduncle;

FIG. 2.2; Juvenile leaf exhibiting anthocyanin;

FIG. 2.3; Semi-juvenile leaf;

FIG. 2.4; Cluster of flower buds showing attachment to stem;

FIG. 2.5; Bare mature stem exhibiting thorns, as well as a bare juvenile stem exhibiting anthocyanin;

FIG. 2.6; Fully mature leaf.

DETAILED DESCRIPTION OF THE VARIETY

The following is a description of 'Poulen012', as observed in its growth in a field nursery in Jackson County, Oreg. Observed plants are 3 years of age. Plants were grown on *Rosa multiflora* understock. Color references are made using The Royal Horticultural Society (London, England) Colour Chart, 1995, except where common terms of color are used.

For a comparison, several physical characteristics of the rose variety 'Poulen009', a rose variety from the same inventors described and illustrated in U.S. Plant patent application Ser. No. 10/742,402 dated Dec. 22, 2003 are compared to 'Poulen012' in Chart 1.

CHART 1

| | 'Poulen012' | 'Poulen009' |
|---|---|---|
| General tonality of open flower | Red Group 49B to 49C | On open flower Red Group 54D with intonations of Red Group 52C. |
| Petalage | 45 to 50 petals | 45 petals |
| Peduncle length | 45 to 50 mm | 40 to 45 mm |
| Filament color | Greyed-Orange Group 163B | Yellow-Orange Group 18A |

FLOWER AND FLOWER BUD

Blooming habit: Recurrent.

Flower bud:

*Size.*—Upon opening, 28 mm in length from base of receptacle to end of bud. Bud diameter is 17 mm.

*Bud form.*—Pointed ovoid.

*Bud color.*—As sepals unfold, petals are Orange Group 26A to 26B with intonations of Red-Purple Group 59A and Red Group 53B. At ¼ opening petals are Orange Group 29C to Red Group 52D with intonations of Red Group 53C.

*Sepals.*—Upper Surface: Color: Yellow-Green Group 144B. Anthocyanic pigments the color of Greyed-Red Group 178A. Surface: Strongly pubescent. Lower Surface: Color: Yellow-Green Group 144A. Anthocyanic pigments the color of Greyed-Red Group 178A observed. Texture: Smooth with scant stipitate glands. Sepal Shape: Sepal apex is cirrhose. Base is flat at union with receptacle. Sepal Margin: Margins have weak foliaceous appendages on three of the five sepals. Size: 21 mm (10)×9 mm (w). Shape: Linear with acute apex.

*Receptacle.*—Surface: Smooth. Shape: Urn-shaped. Size: 8 mm (h)×10 mm (w). Color: Yellow-Green Group 144A. Anthocyanic pigments the color of Greyed-Red Group 181A observed.

*Peduncle.*—Surface: Smooth. Length: 45 to 50 mm. Color: Yellow-Green Group 144B. Anthocyanic pigments the color of Greyed-Orange Group 175B observed. Strength: Strong.

*Borne.*—In clusters of 3 flower buds per stem.

Flower bloom:

*Fragrance.*—Strong perfumed scent.

*Duration.*—The blooms have a duration on the plant of approximately 10 to 14 days. After flowers have fully matured, petals fall cleanly away from plant.

*Size.*—Flower diameter is 70 to 100 mm when open. Flower depth is 45 mm on average.

*Form.*—General flower shape is a deep cup with tight high centers. Shape of flower when viewed from the side: Upon opening, upper part: Flat. Upon opening, lower part: Flat. Open flower, upper part: Flat. Open flower, lower part: Concave.

Petalage: On average 45 to 50 petals under normal conditions with 7 petaloids.

Color:

*Upon opening, petals.*—Outermost petals: Outer side: Orange Group 27D with intonations of Red Group 39C and Red-Purple Group 68D at petal margins. Inner Side: White Group 155B at basal zone with an overlay of Red Group 49A to 49B from middle zone to marginal zone. Innermost petals: Outer side: Yellow-Orange Group 19C with intonations of Red Group 49A to 49B at margins. Inner Side: Yellow-Orange Group 19C with intonations of Red Group 49A to 49B at margins.

*Upon opening, basal petal spots.*—Outermost petals: Outer side: Yellow Group 4A. Inner Side: Yellow Group 6C. Innermost petals: Outer side: Yellow Group 4A. Inner Side: Yellow Group 6C.

*After opening, petals.*—Outermost petals: Outer side: White Group 155B with an overlay of Red Group 36D to Red Group 49D. Inner side: White Group 155B with an overlay of Red Group 49C at middle to marginal zones. Innermost petals: Outer side: White Group 155B with an overlay of Red Group 36D to Red Group 49D. Inner Side: Yellow-White Group 158D with intonations of Red Group 49C at marginal zone.

*After opening, basal petal spots.*—Outermost petals: Outer Side: Yellow Group 4B. Inner Side: Yellow Group 6C. Innermost petals: Outer Side: Yellow Group 4B. Inner Side: Yellow Group 6C.

General tonality: On open flower Red Group 49B to 49C. No change in the general tonality at the end of the $10^{th}$ day.

Petals:

*Petal reflex.*—Somewhat reflexed.

*Margin.*—Entire and uniform. Weak to medium undulations of margin observed.

*Shape.*—Apex: Round. Base: Acute.

*Size.*—47 to 55 mm (l)×40 to 50 mm (w).

*Texture.*—Smooth.

*Thickness.*—Thick.

*Arrangement.*—Formal.

Petaloids:

*Quantity.*—6 to 10.

*Color.*—Upper surface: Red Group 49C. Lower Surface: Orange Group 27D to Red Group 49B.

*Size.*—35 mm (l)×15 mm (w).

*Shape.*—Irregular. Bas is acute. Apex is round.

Reproductive organs:

*Pistils.*—Length: 5 mm. Quantity: 88 (actual count).

*Pollen.*—None Observed.

*Anthers.*—Size: 3 mm in length. Color: Greyed-Yellow Group 162C. Quantity: 107 (actual count).

*Filaments.*—Color: Greyed-Orange Group 163B. Length: 7 mm.

*Stigmas.*—Inferior relative to the length of filaments and the height of the anthers. Color: Greyed-Yellow Group 162B.

*Styles.*—Color: Yellow-Green Group 150D. Other Intonations: Red Group 39B.

*Hips.*—None Observed in the field nursery in Jackson County, Oreg.

PLANT

Plant growth: Vigorous, upright to bushy. When grown as a budded field grown plant on *Rosa multiflora* understock, the average height of the plant is 75 cm and the average width is 75 cm.

Stems:

*Color.*—Young wood: Greyed-Red Group 181A. Older wood: Yellow-Green Group 144B.

*Surface texture.*—Young wood: Smooth. Older wood: Smooth.

Thorns:

*Incidence.*—4 thorns per 10 cm of stem.

*Size.*—Average length: 7 mm.

*Color.*—Greyed-Red Group 181A.

*Shape.*—Concave.

Plant foliage: Normal number of leaflets on normal leaves in middle of the stem: 5 to 7 leaflets.

*Compound leaf size.*—150 mm (l)×135 mm (w).

*Color.*—Mature Foliage: Upper surface: Yellow-Green Group 147A. Lower surface: Yellow-Green Group 147C. Juvenile foliage: Upper surface: Red-Purple Group 187A. Lower surface: Red-Purple Group 187B. Anthocyanin: Location: New leaves. Color: Greyed-Purple Group 187A to Greyed-Red Group 181A.

Plant leaves and leaflets:

*Stipules.*—Size: 20 mm in length. Quantity: 2 per compound leaf. Shape: Linear with outward extending apecies. Margins: Finely serrated with medium quantity of stipitate glands. Color: Greyed-Red Group 182A.

*Petiole.*—Length: 32 mm. Color: Yellow-Green Group 144B. Anthocyanin: Greyed-Red Group 182A. Underneath: Thorns, stipitate glands, and light pubescence.

*Rachis.*—Length: 45 mm. Color: Yellow-Green Group 144B. Anthocyanin: Greyed-Red Group 182A. Underneath: Thorns, stipitate glands, and light pubescence.

*Leaflet.*—Edge: Serrated. Size: Terminal leaflets are 65 mm in length by 52 mm wide on average. Shape: Generally rounded to ovate. Leaf apecies are cuspidate. Leaf bases are round. Texture: Smooth. Thickness: Thick. Arrangement: Odd pinnate. Venation: Reticulate. Glossiness: Matte finish.

Disease resistance: Above average resistance to mildew, rust, black spot, and Botrytis under normal growing conditions in Jackson County, Oreg.

Cold hardiness: The variety 'Poulen012' has been found to be cold tolerant to USDA Cold Hardiness Zone 6.

We claim:

1. A new and distinct variety of rose plant of the hybrid tea rose class named 'Poulen012', substantially as herein illustrated and described as a distinct and novel rose variety due to its abundant pink flowers, disease resistance, and extended period of bloom.

* * * * *

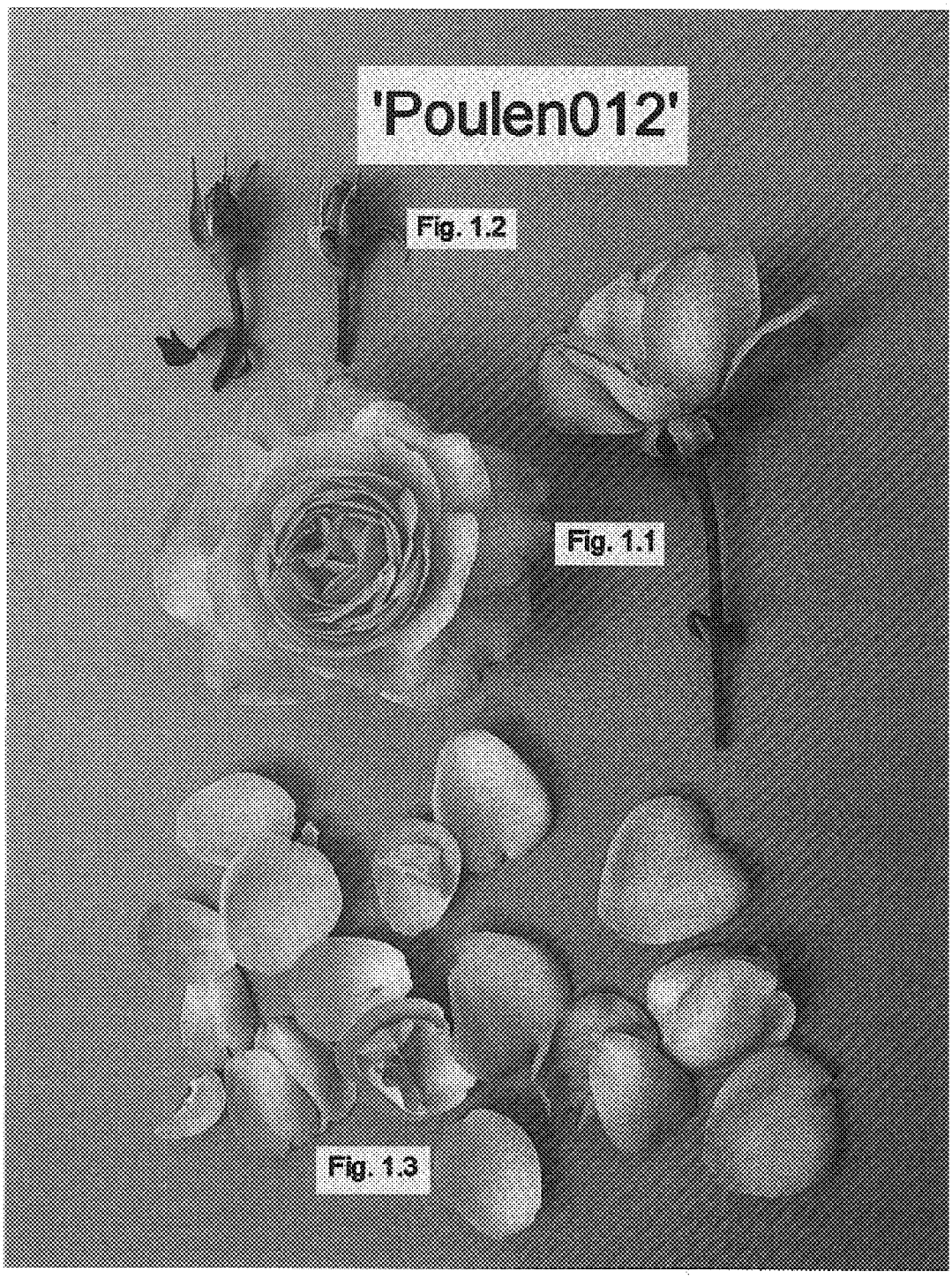
'Poulen012'
Fig. 1.2
Fig. 1.1
Fig. 1.3

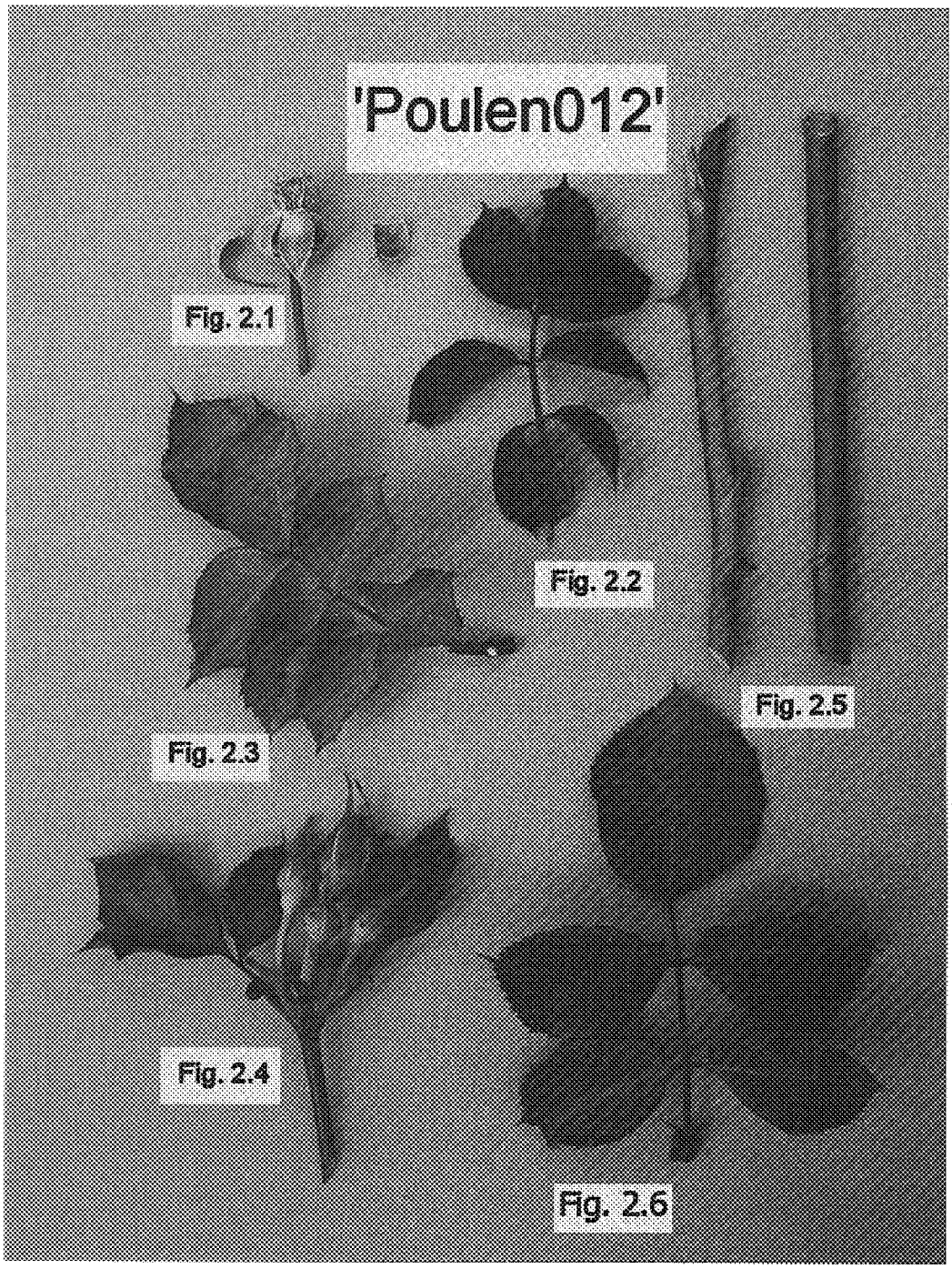
'Poulen012'
Fig. 2.1
Fig. 2.2
Fig. 2.3
Fig. 2.4
Fig. 2.5
Fig. 2.6